(12) United States Patent
Kivi et al.

(10) Patent No.: US 8,138,151 B2
(45) Date of Patent: Mar. 20, 2012

(54) PEPTIDES

(75) Inventors: Elina Kivi, Freiburg (DE); Kati Elima, Turku (FI); Sirpa Jalkanen, Piispanristi (FI)

(73) Assignee: Faron Ventures Oy, Turku (FI)

( * ) Notice: Subject to any disclaimer, the term of this patent is extended or adjusted under 35 U.S.C. 154(b) by 406 days.

(21) Appl. No.: 12/517,898

(22) PCT Filed: Dec. 18, 2007

(86) PCT No.: PCT/FI2007/000296
§ 371 (c)(1),
(2), (4) Date: Jun. 5, 2009

(87) PCT Pub. No.: WO2008/077993
PCT Pub. Date: Jul. 3, 2008

(65) Prior Publication Data
US 2010/0316569 A1    Dec. 16, 2010

(30) Foreign Application Priority Data

Dec. 27, 2006  (FI) .................................... 20061156

(51) Int. Cl.
*A61K 38/08*    (2006.01)
(52) U.S. Cl. ......................................... 514/15; 530/328
(58) Field of Classification Search .................. None
See application file for complete search history.

(56) References Cited

FOREIGN PATENT DOCUMENTS

| WO | 93/25582 A1 | 12/1993 |
| WO | 02/02090 A2 | 1/2002 |
| WO | 2006/128951 A1 | 12/2006 |

OTHER PUBLICATIONS

Vainio, P.J. et al., "Safety of Blocking Vascular Adhesion Protein-1 in Patients with Contact Dermatitis," © Basic & Clinical Pharmacology & Toxicology, 2005, vol. 96, pp. 429-435.
Yegutkin, G.G., "A Peptide Inhibitor of Vascular Adhesion Protein-1 (VAP-1) Blocks Leukocyte-Endothelium Interactions Under Shear Stress," 2004, Eur. J. Immunol., vol. 34, pp. 2276-2285, © 2004 Wiley-VCH Verlag GmbH & Co. KGaA, Weinheim.
Jaakkola, K. et al., "In Vivo Detection of Vascular Adhesion Protein-1 in Experimental Inflammation," American Journal of Pathology, vol. 157, No. 2, Aug. 2000, pp. 463-471, © American Society for Investigative Pathology.
Wang, E.Y. et al., "Design, Synthesis, and Biological Evaluation of Semicarbazide-Sensitive Amine Oxidase (SSAO) Inhibitors with Anti-Inflammatory Activity," Journal of Medicinal Chemistry, 2006, vol. 49, No. 7, pp. 2166-2173, © 2006 American Chemical Society.

*Primary Examiner* — Cecilia J Tsang
*Assistant Examiner* — Satyanarayana R Gudibande
(74) *Attorney, Agent, or Firm* — Rothwell, Figg, Ernst & Manbeck P.C.

(57) ABSTRACT

This invention relates to novel peptides, discovered by using phage display technique, that bind to VAP-1 (Vascular Adhesion Protein-1). The invention concerns also peptides useful as VAP-1 ligands. Such peptides constitute a portion of natural proteins that are present in the individual. The invention relates particularly to a peptide chain in the leukocyte surface protein, where said peptide chain is useful as a ligand for the VAP-1 molecule and thus facilitates the binding of leukocytes to the vascular endothelium. Furthermore, the invention relates to pharmaceutical and diagnostic compositions for targeting VAP-1 in vivo.

10 Claims, 6 Drawing Sheets

SEQUENCE LISTING

<160> NUMBER OF SEQ ID NOS: 24

<210> SEQ ID NO 1
<211> LENGTH: 10
<212> TYPE: PRT
<213> ORGANISM: Artificial
<220> FEATURE:
<223> OTHER INFORMATION: Phage display library peptide

<400> SEQUENCE: 1

Cys Val Lys Trp Arg Gly Val Val Val Cys
1               5                   10

<210> SEQ ID NO 2
<211> LENGTH: 10
<212> TYPE: PRT
<213> ORGANISM: Artificial
<220> FEATURE:
<223> OTHER INFORMATION: Phage display library peptide

<400> SEQUENCE: 2

Cys Trp Ser Phe Arg Asn Arg Val Leu Cys
1               5                   10

<210> SEQ ID NO 3
<211> LENGTH: 16
<212> TYPE: PRT
<213> ORGANISM: Homo sapiens

<400> SEQUENCE: 3

Cys Ala Arg Leu Ser Leu Ser Trp Arg Gly Leu Thr Leu Cys Pro Ser
1               5                   10                  15

<210> SEQ ID NO 4
<211> LENGTH: 16
<212> TYPE: PRT
<213> ORGANISM: Homo sapiens

<400> SEQUENCE: 4

Cys Ala Thr Leu Ser Trp Val Leu Gln Asn Arg Val Leu Ser Ser Cys
1               5                   10                  15

<210> SEQ ID NO 5
<211> LENGTH: 17
<212> TYPE: PRT
<213> ORGANISM: Homo sapiens

<400> SEQUENCE: 5

Cys Leu Glu Asn Phe Ser Lys Trp Arg Gly Ser Val Leu Ser Arg Arg
1               5                   10                  15

Cys

<210> SEQ ID NO 6
<211> LENGTH: 42
<212> TYPE: DNA
<213> ORGANISM: Artificial
<220> FEATURE:
<223> OTHER INFORMATION: Oligonucleotide primer

<400> SEQUENCE: 6
taatacgact cactataggg caagctgata aaccgataca at          42

<210> SEQ ID NO 7
<211> LENGTH: 24
<212> TYPE: DNA
<213> ORGANISM: Artificial
<220> FEATURE:
<223> OTHER INFORMATION: Oligonucleotide primer

<400> SEQUENCE: 7
ccctcatagt tagcgtaacg atct                              24

<210> SEQ ID NO 8
<211> LENGTH: 9
<212> TYPE: PRT
<213> ORGANISM: Homo sapiens

```
<400> SEQUENCE: 8

Cys Val Lys Trp Arg Gly Val Val Val
1               5

<210> SEQ ID NO 9
<211> LENGTH: 9
<212> TYPE: PRT
<213> ORGANISM: Homo sapiens

<400> SEQUENCE: 9

Cys Val Ser Trp Arg Gly Ala Thr Ile
1               5

<210> SEQ ID NO 10
<211> LENGTH: 9
<212> TYPE: PRT
<213> ORGANISM: Homo sapiens

<400> SEQUENCE: 10

Val Lys Trp Arg Gly Val Val Val Cys
1               5

<210> SEQ ID NO 11
<211> LENGTH: 9
<212> TYPE: PRT
<213> ORGANISM: Homo sapiens

<400> SEQUENCE: 11

Leu Ser Trp Arg Gly Leu Thr Leu Cys
1               5

<210> SEQ ID NO 12
<211> LENGTH: 8
<212> TYPE: PRT
<213> ORGANISM: Homo sapiens

<400> SEQUENCE: 12

Val Lys Trp Arg Gly Val Val Val
1               5

<210> SEQ ID NO 13
<211> LENGTH: 7
<212> TYPE: PRT
<213> ORGANISM: Homo sapiens

<400> SEQUENCE: 13

Lys Trp Arg Gly Val Val Val
1               5

<210> SEQ ID NO 14
<211> LENGTH: 4
<212> TYPE: PRT
<213> ORGANISM: Homo sapiens

<400> SEQUENCE: 14

Lys Trp Arg Gly
1

<210> SEQ ID NO 15
<211> LENGTH: 7
<212> TYPE: PRT
<213> ORGANISM: Homo sapiens

<400> SEQUENCE: 15
```

```
Lys Trp Arg Gly Leu Leu Val
1               5

<210> SEQ ID NO 16
<211> LENGTH: 7
<212> TYPE: PRT
<213> ORGANISM: Homo sapiens

<400> SEQUENCE: 16

Lys Trp Arg Gly Ser Val Leu
1               5

<210> SEQ ID NO 17
<211> LENGTH: 10
<212> TYPE: PRT
<213> ORGANISM: Homo sapiens

<400> SEQUENCE: 17

Cys Trp Asn Tyr Arg His Glu Pro Leu Cys
1               5                   10

<210> SEQ ID NO 18
<211> LENGTH: 8
<212> TYPE: PRT
<213> ORGANISM: Homo sapiens

<400> SEQUENCE: 18

Trp Ser Phe Arg Asn Arg Val Leu
1               5

<210> SEQ ID NO 19
<211> LENGTH: 7
<212> TYPE: PRT
<213> ORGANISM: Homo sapiens

<400> SEQUENCE: 19

Trp Ser Phe Arg Asn Arg Val
1               5

<210> SEQ ID NO 20
<211> LENGTH: 7
<212> TYPE: PRT
<213> ORGANISM: Homo sapiens

<400> SEQUENCE: 20

Trp Ser Phe Lys Asn Arg Val
1               5

<210> SEQ ID NO 21
<211> LENGTH: 4
<212> TYPE: PRT
<213> ORGANISM: Homo sapiens

<400> SEQUENCE: 21

Asn Arg Val Leu
1

<210> SEQ ID NO 22
<211> LENGTH: 8
<212> TYPE: PRT
<213> ORGANISM: Homo sapiens

<400> SEQUENCE: 22

Trp Val Leu Gln Asn Arg Val Leu
1               5
```

```
<210> SEQ ID NO 23
<211> LENGTH: 6
<212> TYPE: PRT
<213> ORGANISM: Homo sapiens

<400> SEQUENCE: 23

Ser Phe Arg Asn Arg Val
1               5

<210> SEQ ID NO 24
<211> LENGTH: 6
<212> TYPE: PRT
<213> ORGANISM: Homo sapiens

<400> SEQUENCE: 24

Ser Phe Lys Asn Arg Val
1               5
```

PEPTIDES

CROSS-REFERENCE TO RELATED APPLICATION

The present application is a national stage filing under 35 U.S.C. §371 of PCT/FI2007/000296, filed Dec. 18, 2007, which in turn claims priority to FI 20061156, filed Dec. 27, 2006, each of which are incorporated herein by reference.

FIELD OF THE INVENTION

This invention relate to novel peptides, discovered by using phage display technique. Said peptides bind to VAP-1 (Vascular Adhesion Protein-1). The invention also relates to peptides which are useful as VAP-1 ligands and which form a portion of natural proteins that occur in individuals. Furthermore, the invention relates to pharmaceutical and diagnostic compositions for targeting VAP-1 in vivo.

BACKGROUND OF THE INVENTION

The publications and other materials used herein to illuminate the background of the invention, and in particular, cases to provide additional details respecting the practice, are incorporated by reference.

VAP-1 is a human endothelial cell adhesion molecule that has several unique properties that distinguish it from the other inflammation-related adhesion molecules. It has a unique and restricted expression pattern and mediates lymphocyte binding to vascular endothelium (Salmi, M., and Jalkanen, S., Science 257:1407-1409 (1992)). Inflammation induces the upregulation of VAP-1 to the surface of vascular endothelial cells mediating leukocyte entry to skin, gut and, inflamed synovium (Salmi, M., and Jalkanen, S., Science 257:1407-1409 (1992); Salmi, M, et al., J. Exp. Med. 178:2255-2260 (1993); Arvilommi, A., et al., Eur. J. Immunol. 26:825-833 (1996); Salmi, M., et al., J. Clin. Invest. 99:2165-2172 (1997): (Salmi. M., and Jalkanen, S., J. Exp. Med. 183:569-579 (1996); J. Exp. Med 186:589-600 (1997)). One of the most interesting features of VAP-1 is a catalytic extracellular domain which contains a monoamine oxidase activity (Smith, D. J., et al., J. Exp. Med 188:17-27 (1998)).

The cloning and sequencing of the human VAP-1 cDNA revealed that it encodes a transmembrane protein with homology to a class of enzymes called the copper-containing amine oxidases (E.C. 1.4.3.6). Enzyme assays have shown that VAP-1 possesses a monoamine oxidase (MAO) activity which is present in the extracellular domain of the protein (Smith, D. J., et al., J. Exp. Med 188:17-27 (1998)). Thus, VAP-1 is an ecto-enzyme. Analysis of the VAP-1 MAO activity showed that VAP-1 belongs to the class of membrane-bound MAO's termed semicarbazide-sensitive amine oxidases (SSAO). These are distinguished from the widely distributed mitochondrial MAO-A and B flavoproteins by amino acid sequence, cofactor, substrate specificity and sensitivity to certain inhibitors. However, certain substrates and inhibitors are common to both SSAO and MAO activities.

Leukocyte trafficking from blood to tissues is not only a prerequisite for generating normal immune responses against microbes but it is also needed for immunosurveillance against malignantly transformed cells. Normally leukocytes leave the blood using a multistep extravasation cascade involving many activation and adhesion molecules both on the leukocyte and on the endothelial lining. VAP-1 is one endothelial molecule that supports rolling, firm adhesion, and transmigration of various subsets of leukocytes into sites of inflammation (Salmi, M., and S. Jalkanen. 2005. Nat. Rev. Immunol. 5:760-771). VAP-1 belongs to semicarbazide sensitive amine oxidases, which are enzymes that catalyze oxidative deamination of amines into corresponding aldehydes in a reaction that also produces hydrogen peroxide and ammonium. The adhesive role of VAP-1 in leukocyte trafficking can be inhibited using function-blocking mAbs or enzyme inhibitors in multiple in vitro and in vivo inflammation models (Salmi, M., and S. Jalkanen. 2005. Nat. Rev. Immunol. 5:760-771). The anti-VAP-1 antibodies do not inhibit the enzymatic activity of VAP-1, and the enzyme inhibitors do not alter the mAb-defined surface epitopes of VAP-1 (Koskinen, K., P. J. Vainio, D. J. Smith, M. Pihlavisto, S. Yla-Herttuala, S. Jalkanen, and M. Salmi. 2004. Blood 103:3388-3395; Bonder, C., M. G. Swain, L. D. Zbytnuik, M. U. Norman, J. Yamanouchi, P. Santamaria, M. Ajuebor, M. Salmi, S. Jalkanen, and P. Kubes. 2005. Immunity 23:153-163). It is thus thought that VAP-1 is involved in leukocyte extravasation by serving as a traditional adhesion molecule (mAb-defined epitopes) and as an enzyme (by reacting with surface displayed amines of leukocytes) (Salmi, M., and S. Jalkanen. 2005. Nat. Rev. Immunol. 5:760-771).

Various strategies for inhibiting VAP-1 activity have been disclosed. For example, WO 93/25582 discloses a monoclonal antibody specifically binding to VAP-1. WO 2003/093319 describes a humanized anti-VAP-1 monoclonal antibody.

Alternatively, VAP-1 can be counteracted by using small molecules as inhibitors. The patent publications WO 2002/020290, WO 2002/002541, WO 2003/006003 and WO 2005/080319 disclose certain hydrazino compounds useful as specific VAP-1 SSAO inhibitors that modulate VAP-1 activity. These compounds are described as useful for the treatment of acute and chronic inflammatory conditions or diseases as well as diseases related to carbohydrate metabolism, aberrations in adipocyte differentiation or function and smooth muscle cell function, and various vascular diseases.

WO 2006/128951 discloses the conjugation of a small molecule inhibitor to a peptide capable of binding to VAP-1, where the peptide has a sequence of 7 to 9 amino acids, and where at least one lysine residue is located in the mid-portion of the sequence.

SUMMARY OF THE INVENTION

The object of this invention is to define VAP-1 ligands. By use of phage libraries, the structure of VAP-1 binding peptides has been clarified. The specifically bound phage inserts were sequenced, and the amino acid sequences were compared to protein data banks. Longer peptides of the most important target proteins were also tested with respect to their ability to bind to VAP-1. The object is particularly to localize a peptide chain in a leukocyte surface protein, where the peptide chain operates as a ligand for the VAP-1 molecule and thus facilitates the binding of leukocytes to the vascular endothelium.

Another object of the present invention is to provide a diagnostic composition useful for in vivo location of VAP-1. The knowledge of the precise location of an amine oxidase will be useful to specifically direct the various treatment methods and other measures to the tissues in which the amine oxidase occur.

A further object is to provide a pharmaceutical composition having a carrier specifically targeting said VAP-1. A therapeutically active agent conjugated to the carrier is useful for exact local treatment of tissues influenced by VAP-1 and the pharmaceutical composition is thus aimed for exact local treatment or prevention of VAP-1 related diseases or disorders.

Thus, in one aspect, the invention concerns a novel peptide having the amino acid sequence CVKWRGVVVC (SEQ ID NO. 1) or CWSFRNRVLC (SEQ ID NO. 2).

In another aspect, the invention concerns a peptide showing a homology of at least 4 amino acids to the amino acid sequence of the peptide having the amino acid sequence CVKWRGVVVC (SEQ ID NO. 1) or CWSFRNRVLC (SEQ ID NO. 2).

In a third aspect, the invention concerns a peptide constituting a portion of a natural protein that is present in an individual, wherein said peptide is CVKWRGVVVC (SEQ ID NO. 1) or CWSFRNRVLC (SEQ ID NO. 2), or shows a homology of at least 4 amino acids to the amino acid sequence of the peptide CVKWRGVVVC (SEQ ID NO. 1) or CWSFRNRVLC (SEQ ID NO. 2).

In a fourth aspect, this invention concerns a diagnostic composition for targeting VAP-1 enzyme in vivo, said composition comprising a labelled peptide, wherein said peptide is as defined above or a modification thereof.

According to a fifth aspect, the invention concerns a method for diagnosing VAP-1 related diseases or conditions in a mammal in vivo, said method comprising administering to the mammal a composition according to this invention, and detecting the label.

According to a sixth aspect, the invention concerns a pharmaceutical composition for use to modulate the activity of VAP-1 enzyme, wherein said composition comprises
i) a peptide as defined above or modified, or
ii) a peptide as defined above or modified, said peptide being further is conjugated to a therapeutically active agent.

According to a seventh aspect, the invention concerns a method for the treatment of or prevention of a VAP-1 related disease or condition in a mammal, said method comprising administering to the mammal a pharmaceutical composition according to this invention.

DETAILED DESCRIPTION OF THE INVENTION

Definitions

Figure 1:
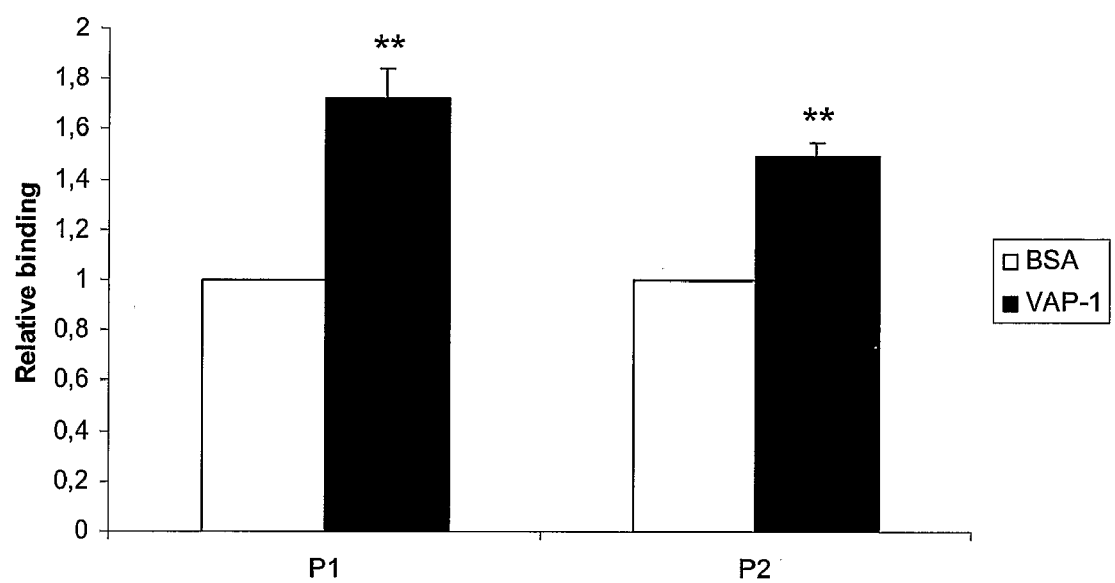
FIG. 1. Two peptides selected from phage display library binds to VAP-1. (A) Phages were selected using wells coated with recombinant VAP-1. Specifically bound phages were eluted from the wells with low pH and bacteria were infected with those phages. Randomly picked phage clones after third and fourth round of panning were sequenced. Number of clones encoding the same peptide are shown in parentheses. (B) Biotinylated synthetic peptides matching to sequences derived from the phages binding to VAP-1 bound to VAP-1. Bound peptides were detected with a streptavidin conjugated secondary reagent. The results are mean±SEM from three separate experiments and triplicate wells in each experiment. **$P<0.01$.

The term "treatment" or "treating" shall be understood to include complete curing of a disease or condition, as well as amelioration or alleviation of said disease or condition.

The term "prevention" shall be understood to include complete prevention, prophylaxis, as well as lowering, the individual's risk of falling ill with said disease or condition.

The term "mammal" refers to a human or animal subject.

The term "therapeutically active agent agent" shall here be understood to cover any geometric isomer, stereoisomer, diastereoisomer, racemate or any mixture of isomers, and any pharmaceutically acceptable salt of the compound.

Preferable Peptides:

The invention is based on a phage display study performed with a peptide library displaying CX8C inserts, where X is any amino acid and C is cysteine. The cysteine units form a sulfur bridge so as to provide a cyclic peptide. The phage vector used was fUSE5, which is an fd phage derivative. The gene sequence of the peptides was joined to the gene of pIII surface protein and therefore the phage pIII surface proteins are fusion proteins.

The amplified primary library was allowed to interact with the target protein VAP-1. Specifically bound phages were amplified in bacteria and the phages were precipitated. The inserts of specifically bound phages were sequenced and the amino acid sequences were compared to protein data bases.

The sequencing gave two peptides, CVKWRGVVVC (SEQ ID NO. 1) and CWSFRNRVLC (SEQ ID NO. 2), with specific binding to VAP-1. According to the results shown below, we believe that specific binding to VAP-1 is not restricted to these specific sequences only. Instead, any peptide showing a homology of at least 4 amino acids, preferably 5, 6, 7, 8 or 9 amino acids, to the amino acid sequence of the peptide CVKWRGVVVC (SEQ ID NO. 1) or CWSFRNRVLC (SEQ ID NO. 2).

The VAP-1 ligand can be a peptide constituting a portion of a natural protein that is present in an individual, where the peptide is CVKWRGVVVC (SEQ ID NO. 1) or CWSFRNRVLC (SEQ ID NO. 2), or is a peptide showing a homology of at least 4 amino acids to the amino acid sequence of the peptide CVKWRGVVVC (SEQ ID NO. 1) or CWSFRNRVLC (SEQ ID NO. 2).

The natural protein is preferably a leukocyte surface protein.

Especially preferable groups of natural proteins are the Siglec group, such as Siglec-9 or Siglec-10; or the ADAM group, such as ADAM28; or the CD58 glycoprotein.

Particularly interesting peptides are CARLSLSWRGLTL-CPS (SEQ ID NO. 3) which is a portion of the Siglec-9 protein; CATLSWVLQNRVLSSC (SEQ ID NO. 4) which is a portion of the Siglec-10 protein; and CLENFSKWRGSV-LSRRC (SEQ ID NO. 5), which is a portion of the ADAM28 protein.

Preferable Labels:

In diagnostic compositions, the label can be any detectable label suitable for use in vivo. Thus, the label could be, for example, a fluorescent label or more preferably, a radioisotope.

Preferable Pharmaceutical Compositions:

Although the peptides as such may be used in therapy, it is believed that modified forms thereof are preferable. Non-modified peptides are known to undergo rapid proteolysis in vivo, they may have difficulties to penetrate biological barriers, poor chemical stability, low aqueous solubility, and they may have a too short half-life in systemic circulation. To overcome such drawbacks, they can, for example be chemically modified or administered as prodrugs. The wording "modification" shall be understood to include also prodrugs of the peptides. Modification of peptides for in vivo use is well known in the art. See for example R Oliyai and V J Stella, Annu. Rev. Pharmacol. Toxicol. 1993, 32:521-44.

The therapeutically active agent conjugated to the peptide can be any drug. Most preferably, the therapeutically active agent is a VAP-1 inhibitor or VAP-1 substrate, especially a VAP-1 inhibitor. If, for example, the peptide as such is a VAP-1 inhibitor, the conjugated therapeutically active agent is also a VAP-1 inhibitor.

The drug molecule can be conjugated to the peptide in manners known as such by using a suitable coupling group. Such groups can e.g. be amino, imino, amido, imido, thio, carbonyl, carboxyl etc. groups and derivatives of said groups. As example of one suitable specific conjugating group can be mentioned 1-ethyl-3-(3-dimethyl-aminopropyl)carbidiimide or N-hydroxysuccinimide, which have been used to couple doxorubicin to peptides (W Arap et al., Science Vol. 279, 16 Jan. 1998, pp. 377-380). If needed, a linker group could also be inserted e.g. between the peptide and the aforementioned coupling group in order to facilitate coupling that otherwise would be difficult due to steric hindrance or other reasons. Such linkers are well known in the art. In its simplest form, the linker can be a hydrocarbon chain of suitable length.

According to another alternative, the drug molecule can be incorporated in a vehicle, such as a particle, especially a liposome or a nanoparticle, particularly a polymeric nanoparticle, having the ability to release the drug molecule at a controlled rate. Thus, conjugation of the drug molecule to the peptide shall be understood to include also this alternative, where the drug molecule is not directly attached to the peptide but instead attached to the peptide via the vehicle.

Combinations of modified peptides and drugs incorporated in nanoparticles are believed to be preferred.

Diseases or Conditions with Responsiveness to Amine Oxidase Inhibitors:

As examples of groups of diseases or conditions the treatment or prevention of which would benefit from inhibiting VAP-1 enzyme can be mentioned inflammatory diseases or conditions; diseases related to carbohydrate metabolism; diseases related to aberrations in adipocyte differentiation or function or smooth muscle cell function and vascular diseases. However, the diseases or conditions are not restricted to these groups.

According to one embodiment, the inflammatory disease or condition can be a connective tissue inflammatory disease or condition, such as, but not limited to ankylosing spondylitis, Reiter's syndrome, psoriatic arthritis, osteoarthritis or degenerative joint disease, rheumatoid arthritis, Sjögren's syndrome, Bechet's syndrome, relapsing polychondritis, systemic lupus erythematosus, discoid lupus erythematosus, systemic sclerosis, eosinophilic fasciitis, polymyositis and dermatomyositis, polymyalgia rheumatica, vasculitis, temporal arteritis, polyarterisis nodosa, Wegner's granulamatosis, mixed connective tissue disease, or juvenile rheumatoid arthritis.

According to another embodiment, said inflammatory disease or condition is a gastrointestinal inflammatory disease or condition, such as, but not limited to Crohn's disease, ulcerative colitis, irritable bowel syndrome (spastic colon), fibrotic conditions of the liver, inflammation of the oral mucosa (stomatitis), or recurrent aphtous stomatitis.

According to a third embodiment, said inflammatory disease or condition is a central nervous system inflammatory disease or condition, such as, but not limited to multiple sclerosis, Alzheimer's disease, or ischemia-reperfusion injury associated with ischemic stroke.

According to a fourth embodiment, said inflammatory disease or condition is a pulmonary inflammatory disease or condition, such as, but not limited to asthma, chronic obstructive pulmonary disease, or adult respiratory distress syndrome.

According to a fifth embodiment, said inflammatory disease or condition is a skin inflammatory disease or condition such as, but not limited to contact dermatitis, atopic dermatitis, psoriasis, pityriasis rosea, lichen planus, or pityriasis rubra pilaris.

According to a sixth embodiment said inflammatory condition is related to tissue trauma or resulting from organ transplantations or other surgical operations.

According to an seventh embodiment, said disease related to carbohydrate metabolism is a disease such as but not limited to diabetes, atherosclerosis, vascular retinopathies, retinopathy, nephropathy, nephrotic syndrome, polyneuropathy, mononeuropathies, autonomic neuropathy, foot ulcers or joint problems.

According to a eighth embodiment said disease relating to aberrations in adipocyte differentiation or function or smooth muscle cell function is a disease such as but not limited to atherosclerosis or obesity.

According to an ninth embodiment, the vascular disease is a disease such as but not limited to atheromatous aterioscleosis, nonatheromateous aterosclerosis, ischemic heart disease, peripheral aterial occlusion, thromboangiitis obliterans (Buerger's disease), or Raynaud's disease and phenomenon.

For the purpose of this invention, the compounds disclosed in this invention or their isomer, isomer mixture or their pharmaceutically acceptable salts can be administered by various routes. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. Suitable oral formulations include e.g. conventional or slow-release tablets and gelatine capsules.

The required dosage of the compounds will vary with the particular disease or condition being treated, the severity of the condition, the duration of the treatment, the administration route and the specific compound being employed.

Thus, a typical dose is in the dosage range of about 0.1 microgram/kg to about 300 mg/kg, preferably between 1.0 microgram/kg to 10 mg/kg body weight. Compounds of the present invention may be administered in a single daily dose, or the total daily dosage may be administered in divided doses of two, three or four times daily.

The invention will be illuminated by the following non-restrictive Experimental Section.

Experimental Section

Materials and Methods

Antibodies and Other Reagents

Monoclonal antibodies TK8-18 and JG2.10 and a polyclonal antibody against human VAP-1 were used. Streptavidin-HRP conjugate was from BD Biosciences (San Jose, Calif., USA), anti-human IgG (Fc-spesific) and FITC conjugated anti-rabbit IgG were from Sigma (St Louis, Mo., USA), Alexa 488 conjugated anti-FITC, Alexa 546 conjugated anti-rat IgG and Prolong Antifade Gold from Molecular probes (Eugene, Oreg., USA). CFSE was from Invitrogen and BM chemiluminescence ELISA substrate was from Roche (Basel, Switzerland). Semicarbazide and clorgyline were purchased from Sigma.

Phage Display Screening

Phage display screening was performed with a peptide library displaying CX8C inserts (where X is any aminoacid and C is cysteine). Recombinant human VAP-1 (100 micrograms/ml TBS) was coated onto Nunc Maxisorp 96-well plates (Fisher Scientific) overnight at 4° C. Non-specific binding sites were blocked with TBS/3% BSA for 2 h at room temperature and washed three times with TBS. The phage library solution ($3 \times 10^9$ TU in TBS/1% BSA) was incubated in the wells for 2 h at room temperature. Thereafter, the wells were washed with TBS/0.1% Tween to remove unbound phages. Specifically bound phages were eluted from the wells with low pH buffer and used to infect K91kan E. coli. After amplification of the phages in bacteria they were purified by precipitation with polyethylene glycol. Three more rounds of panning were performed in the same manner, except that less VAP-1 was coated onto the microtiter wells (5 micrograms and 1 microgram) and the phage library was incubated on the wells only for 1 h at room temperature. For colony sequencing a 1 microliter aliquot was used in PCR with 15 pmol/microliter of the forward primer 5'-TAATACGACTCACTATAGGGCAAGCTGATAAACCGATACAAT-3' (SEQ ID NO. 6) and the reverse primer 5'-CCCTCATAGTTAGCGTAACGATCT-3' (SEQ ID NO. 7). The PCR conditions were 96° C. for 5 min, 92° C. for 30 s, 60° C. for 30 s, 72° C. for 60 s and 72° C. for 4 min and 35 cycles were run. A 1 microliter aliquot of purified PCR product was taken for sequencing using 5 pmol/microliter of either one of the primers.

In Vitro-Binding Assays

Binding of peptides to VAP-1. VAP-1 and BSA as a negative control were immobilized in wells of Nunc Maxisorp 96-well ELISA plate overnight at 4° C., blocked with PBS/3% BSA for 1 h at 37° C. and incubated with biotinylated peptides (10 micrograms/ml or 100 micrograms/ml) for 2 h at room temperature. The wells were washed with PBS/0.1% Tween, incubated with HRP conjugated streptavidin for 1 h at room temperature and after washing a BM chemiluminescence ELISA substrate was added. Luminescence was measured with a luminometer (Tecan Ultra, Tecan, Zürich, Switzerland).

Siglec 10-Fc chimera binding to VAP-1. Anti-human IgG (Fc specific) antibody was coated onto Nunc Maxisorp wells overnight at 4° C. After blocking with PBS/2% BSA, Siglec-10-Ig-chimera (1 microgram/ml) was immobilized to wells via its Fc-tail for 2 h at room temperature and thereafter, recombinant VAP-1 (1 micrograms g/ml and 5 micrograms/10 was incubated in wells for 2 h at room temperature. After washing the wells with PBS/0.1% Tween, biotinylated anti-human VAP-1 antibody (TK-8-18) was incubated in the wells for 1 h at room temperature and after that, the wells were incubated with HRP conjugated streptavidin for 1 h at room temperature. After washing the wells, a BM chemiluminescence ELISA substrate was added to the wells and luminescence was measured with Tecan luminometer.

Cell-based assays. First, CHO-Siglec-10 transfectants and mock controls were detached from the culture flasks by a short trypsin-EDTA treatment and washed once with RPMI 1640+10% FCS. $3 \times 10^5$ CHO-Siglec-10 or CHO-mock cells were incubated with 20 micrograms/ml recombinant VAP-1 for 2 h at 4° C. After incubation the cells were washed once with RPMI 1640+10% FCS and incubated with polyclonal anti-VAP-1 antibody (1:1000) for 1 h at 4° C. The cells were washed once and incubated with FITC-conjugated anti-rabbit IgG (1:1000) (Sigma, St Louis, Mo., USA) secondary antibody for 1 h at 4° C. Thereafter, Alexa 488 conjugated anti-FITC antibody was added to enhance the signal. Binding was determined by analyzing $10^4$ cells with FACSCalibur and Cellquest software (Becton Dickinson, San Jose, Calif., USA).

Second, CHO-VAP-1 and CHO-mock cells were cultured in 96-well cell culture plates and allowed to reach confluence. After blocking the wells with PBS/1% BSA for 20 min at 4° C., $2 \times 10^5$ CFSE-labeled CHO-Siglec-10 cells were added in 50 microliters of RPMI 1640 containing 10% FCS. After a 30-min incubation at 37° C. in 5% $CO^2$, the wells were washed altogether nine times with 100 microliters of RPMI 1640 to remove non-adherent cells. Adherence was quantified by measuring fluorescence with a Tecan fluorometer after each wash.

In certain assays the cells were treated with neuraminidase (Roche, Basel, Switzerland). Cells were suspended in 1 ml of RPMI 1640 containing 10% FCS and treated using 0.1 mU neuraminidase for 1 h at 37° C. and washed with RPMI 1640 thereafter.

Epitope Analysis

Surface stainings of CHO-VAP-1 and CHO-mock cells were performed using anti-VAP-1 (JG2.10) and a negative control (9B5) mAbs. Competitive stainings were done in the presence of 10 micrograms/ml either human Ig or Siglec-10-Ig. Alexa546-conjugated goat anti-rat IgG was used as the secondary reagent. All cells were analyzed using FACSCalibur and Cellquest software.

Isotopic Enzyme Assay

Semicarbazide sensitive mine oxidase (SSAO) enzymatic activity of VAP-1 after interaction with Siglec-10 was determined radiochemically. Briefly, 14-C labeled benzylamine (a model substrate for SSAO) was used as the substrate. The assay was performed at 37° C. for 120 minutes in a final volume of 400 microliters 0.1 mM Krebs-Ringer phosphate glucose buffer (pH 7.35) containing CHO-VAP-1 cell lysate and 5 microM benzylamine with tracer $^{14}$C benzylamine (40 000 dpm) in the presence of 1 mM clorgyline (a MAO inhibitor). In the inhibitory studies, the lysate was preincubated 30 minutes with 10 micrograms/ml or 70 micrograms/ml Siglec-10-Ig-chimera or 1 mM semicarbazide before adding the benzylamine. Catalytic reaction was stopped with citric acid, and the aldehyde reaction products were extracted from the analyzed mixture into toluene containing 0.35 g/L diphenyloxazole. The amount of 14C-labeled benzaldehyde was quantified by scintillation counting using a beta-counter Wallac-1409 (Turku, Finland), and the activity of the enzyme was expressed as picomoles of benzaldehyde formed by milliliter of lysate per hour.

Results

Sequence Analysis

We used the $CX_8C$ phage library to search for ligands for purified recombinant VAP-1 immobilized on 96-well plates. After four rounds of panning we got a 400-fold enrichment of phages bound to VAP-1 in comparison to control, BSA was used as a negative control. The sequencing of randomly selected clones gave two different sequences, CVKWRGVVVC (SEQ ID NO. 1) (peptide P1) and CWSFRNRVLC (SEQ ID NO. 2) (peptide P2) (their binding to VAP-1 shown in FIG. 1A).

The amino acid sequences of the peptides P1 and P2 were subjected to a protein-protein-BLAST (basic local alignment search tool) database search.

In the sequence comparison shown below, the uppermost sequence belongs to the peptide tested, the undermost sequence is the sequence localized in the data base, and the middle line shows the common amino acids. The +-mark means that the amino acids are of the same kind. The numbers refer to the serial number of the amino acids.

A BLAST search for the sequence CVKWRGVVVC (SEQ ID NO. 1) (peptide P1) gave 103 hits. The best hits were:

The variable κ-chain of immunoglobulin

```
  1      CVKWRGVVV        9     (SEQ ID NO. 8)
         CV WRG +
  3      CVSWRGATI       11     (SEQ ID NO. 9)
```

Another interesting hit:
SIGLEC-9 (Sialic Acid-Binding Ig-Like Lectin)

```
  2      VKWRGVVC        10     (SEQ ID NO. 10)
         + WRG+ +C
263      LSWRGLTLC      271     (SEQ ID NO. 11)
```

A BLAST-search for the insert portion only (VKWRGVVV) (SEQ ID NO. 12) of the peptide gave 105 hits. The best hit was
SOS1 (Son of Sevenless)

```
  2      KWRGVVV         8     (SEQ ID NO. 13)
         KWRG++V                (SEQ ID NO. 14)
 18      KWRGLLV        24     (SEQ ID NO. 15)
```

Another interesting hit was:
ADAM28 (a Disintegrin and Metalloprotease)

```
  2      KWRGVVV         8     (SEQ ID NO. 13)
         KWRG V+                (SEQ ID NO. 14)
278      KWRGSVL       284     (SEQ ID NO. 16)
```

A BLAST search for the sequence CWSFRNRVLC (SEQ ID NO. 2) (peptide P2) gave 116 hits. The best hit was:
A Non-Designed Protein

```
  1      CWSFRNRVLC     10     (SEQ ID NO. 2)
         CW++R+  LC
 11      CWNYRHEPLC     20     (SEQ ID NO. 17)
```

A BLAST search for the insert portion only (WSFRNRVL) (SEQ ID NO. 18) of the peptide P2 gave 106 hits. The best hit was:
Light Ear Protein, Isoform D

```
  1      WSFRNRV         7     (SEQ ID NO. 19)
         WSF+NRV
241      WSFKNRV       247     (SEQ ID NO. 20)
```

Other interesting hits were
SIGLEC-10

```
  1      WSFRNRVL        8     (SEQ ID NO. 18)
         W +NRVL                (SEQ ID NO. 21)
288      WVLQNRVL      295     (SEQ ID NO. 22)
```

CD58 or LFA-3

```
  2      SFRNRV          7     (SEQ ID NO. 23)
         SF+NRV
 76      SFKNRV         81     (SEQ ID NO. 24)
```

Longer Peptides

The peptides obtained by phage display CVKWRGVVVC (SEQ ID NO. 1) (peptide P1) and CWSFRNRVLC (SEQ ID NO. 2) (peptide P2) were shown to bind to VAP-1 in an ELISA assay (results shown in FIG. 1A.). Therefore also longer peptides corresponding to amino acid sequences in the proteins were tested. The peptides relate to the target proteins Siglec-9, Siglec-10 and ADAM28:

```
           CWSFRNRVLC                       (SEQ ID NO. 2)
           W  +NRVL                         (SEQ ID NO. 21)
P3 =  CATLSWVLQNRVLSSC = Siglec-10          (SEQ ID NO. 4)

CVKWRGVVVC                       (SEQ ID NO. 1)
           + WRG+ +C
P5 =  CARLSLSWRGLTLCPS = Siglec-9           (SEQ ID NO. 3)

CVKWRGVVVC                       (SEQ ID NO. 1)
           KWRG V+                          (SEQ ID NO. 14)
P6 =  CLENFSKWRGSVLSRRC = ADAM28            (SEQ ID NO. 5)
```

Figure 2:
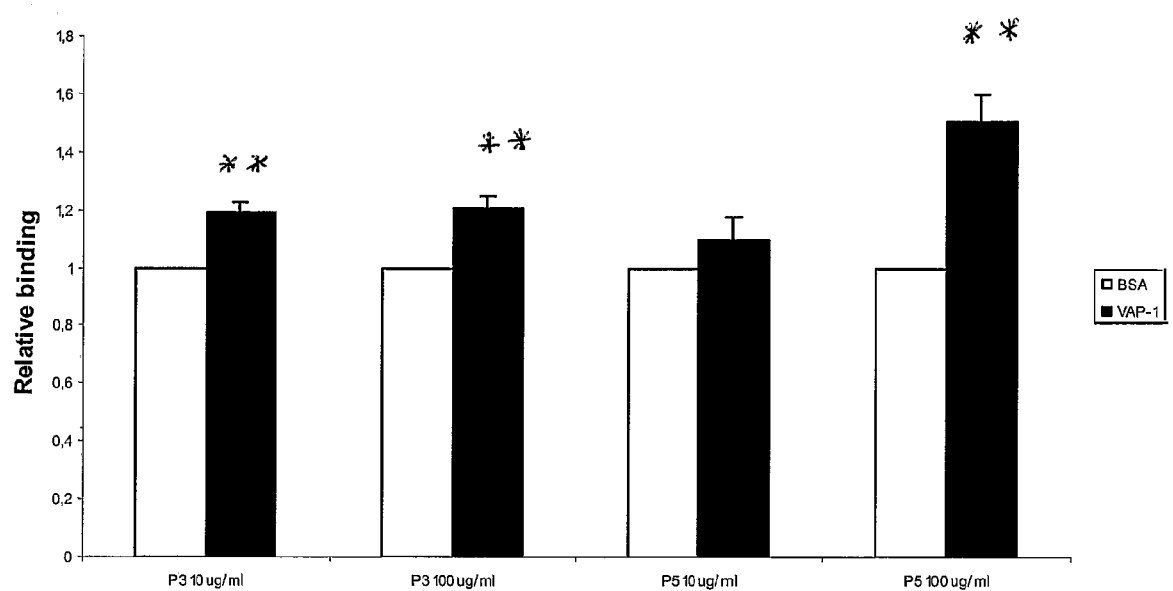
FIG. 2. Two of the longer peptides matching to Siglec 10 amino acid sequence (P3) and Siglec 9 amino acid sequence (P5) binds to VAP-1. Microtiter wells were coated with 1 µg/ml VAP-1 or BSA as a control and peptides with concentrations shown in the figure were incubated in those wells. Binding of the biotinylated peptides was detected with streptavidin conjugated secondary reagent. The results are mean±SEM from three separate experiments and triplicate wells in each experiment. **$P<0.01$.

The binding of all the long peptides P3 and P5 to VAP-1 was tested and the results are shown in FIG. 2.

Screening of a Phage Library for Peptides Binding to VAP-1

To validate the binding of the sequences CVKWRGVVVC (SEQ ID NO. 1) (peptide P1) and CWSFRNRVLC (SEQ ID NO. 2) (peptide P2) to VAP-1 we tested binding of synthetic peptides corresponding to these sequences with ELISA. These studies showed that the peptides efficiently bound to purified recombinant VAP-1 (FIG. 1B).

Sequences derived from the phage library screening revealed short similarities with few proteins expressed at the surface of leukocytes, for example with a short sequence of Sialic acid binding Ig-like lectin, Siglec-10 (residues 288-295). The large extracellular part of Siglec-10 is composed of one Ig-like V-type domain and three Ig-like C2-type domains. The sequence obtained from the phage library is part of the extracellular C2-type domain 2. The V-type domain is known to have a role in interactions between Siglecs and sialic acids, but the role of C2-type domains is unknown.

Next, binding of two longer peptides, P3, which has an amino acid sequence completely matching to Siglec-10 amino acid sequence (residues 284-297), and P5 matching to Siglec-9, to VAP-1 were tested. The sequence of P3 was CATLSWVLQNRVLSSC (SEQ ID NO. 4) (cysteines to both end of the peptide were added, because the original peptide from the phage display screening had the cysteines, thus being circular). The sequence of P5 was CARLSLSWR-GLTLCPS (SEQ ID NO. 3). P3 and P5 bound specifically to wells coated with purified VAP-1 in comparison to BSA (FIG. 2).

In Vitro Binding Assays Show an Interaction Between VAP-1 and Siglec-10

Figure 3A:
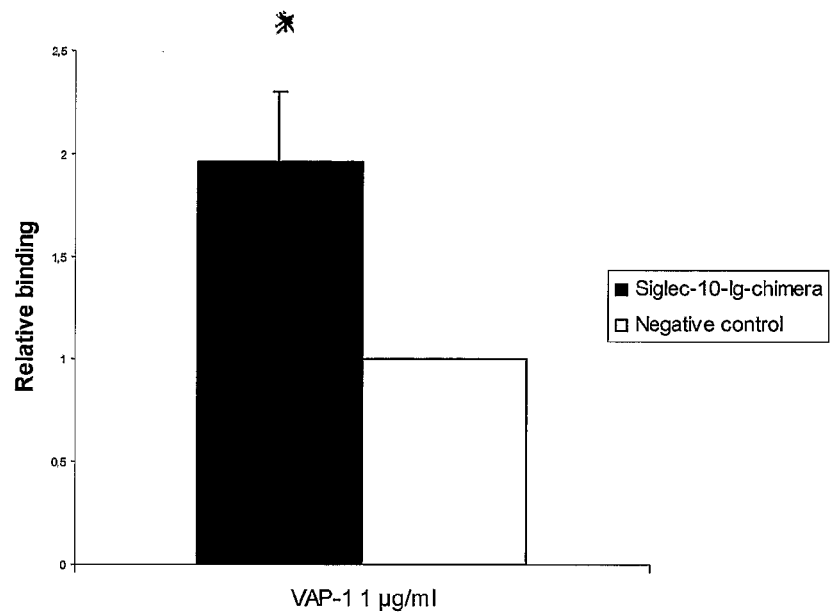
FIG. 3. Siglec-10 is a counter-receptor for VAP-1. (A) ELISA was used to test, whether recombinant VAP-1 binds to Siglec-10-Ig-chimera. Siglec-10-Ig-chimera was immobilized to microtiter wells via anti-human IgG antibody. 1 µg/ml of VAP-1 was incubated in those wells and binding of VAP-1 was measured using biotinylated anti-VAP-1 antibody, TK-8-18, and a secondary antibody, HRP-conjugated streptavidin. The results are means±SEM from three separate experiments each having triplicate wells. (B) Flow cytometry was used to detect the binding of recombinant VAP-1 to cells expressing Siglec-10. 20 µg/ml of VAP-1 was incubated with $3\times10^5$ cells expressing Siglec-10 or with mock transfected control cells and the binding was determined using polyclonal anti-VAP-1 antibody and FITC conjugated secondary antibody. The results are means±SEM of mean fluorescent intensities (MFI) from two separate experiments. (C) Binding of cells expressing Siglec-10 to cells expressing VAP-1. Cells expressing VAP-1 and control cells were plated into 96-well tissue culture plate and grown to confluence. Cells expressing Siglec-10 were labeled with a fluorescent dye and incubated in wells plated with cells expressing VAP-1 and control cells. Binding was detected with a fluorometer. The results are means±SEM of fluorescent intensities (FI) from seven separate experiments each having duplicate wells. *$P<0.05$, $P<0.01$, *$P<0.001$.
Figure 3B:
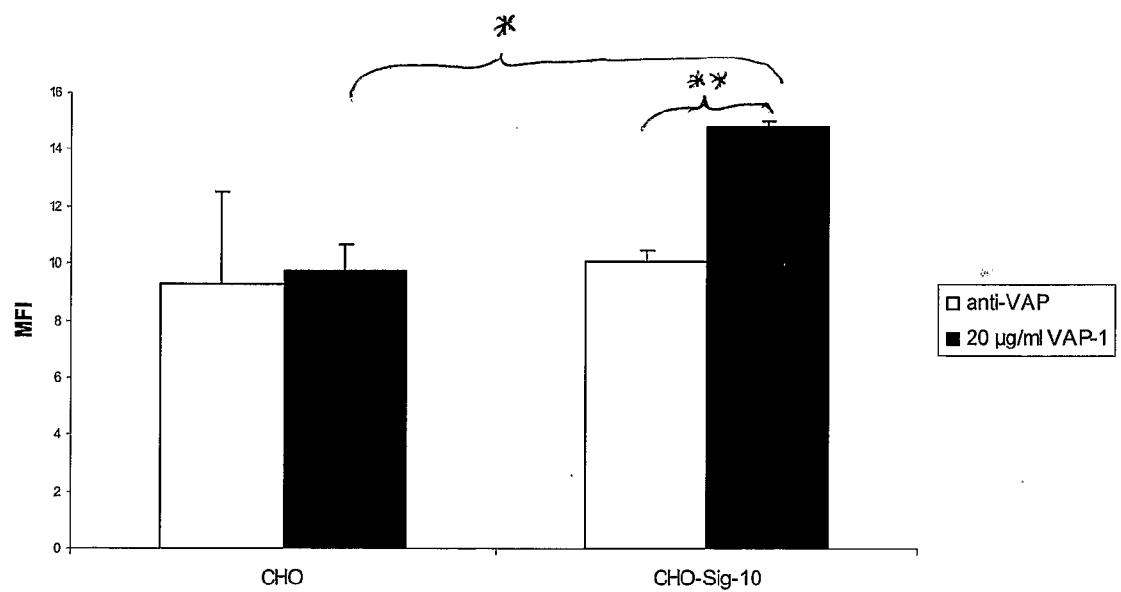
Figure 3C:
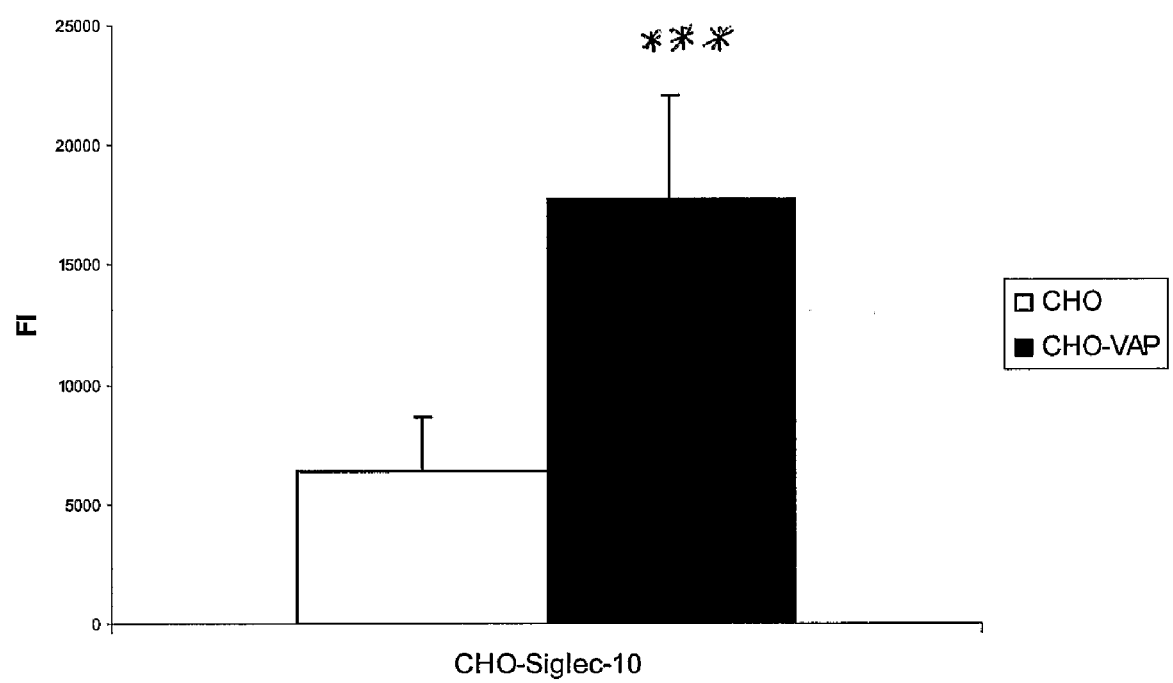

To confirm the initial phage display observation, we next determined whether recombinant VAP-1 interacted with Siglec-10 protein. ELISA studies with purified VAP-1 and Siglec-10-Ig-chimera demonstrated that Siglec-10-Ig-chimera interacts with VAP-1 (FIG. 3A). We also performed another type of binding assay where we tested the binding of recombinant VAP-1 to cells expressing Siglec-10. The results show that recombinant VAP-1 binds to cells expressing Siglec-10 (FIG. 3B). Next, we tested, whether the interaction between cells expressing VAP-1 and cells expressing Siglec-10 take place in VAP-1-Siglec-10 dependent manner. The results were consistent with the previous findings and showed that cells expressing Siglec-10 bound to cells expressing VAP-1 but not to mock transfected cells (FIG. 3C).

Figure 4:
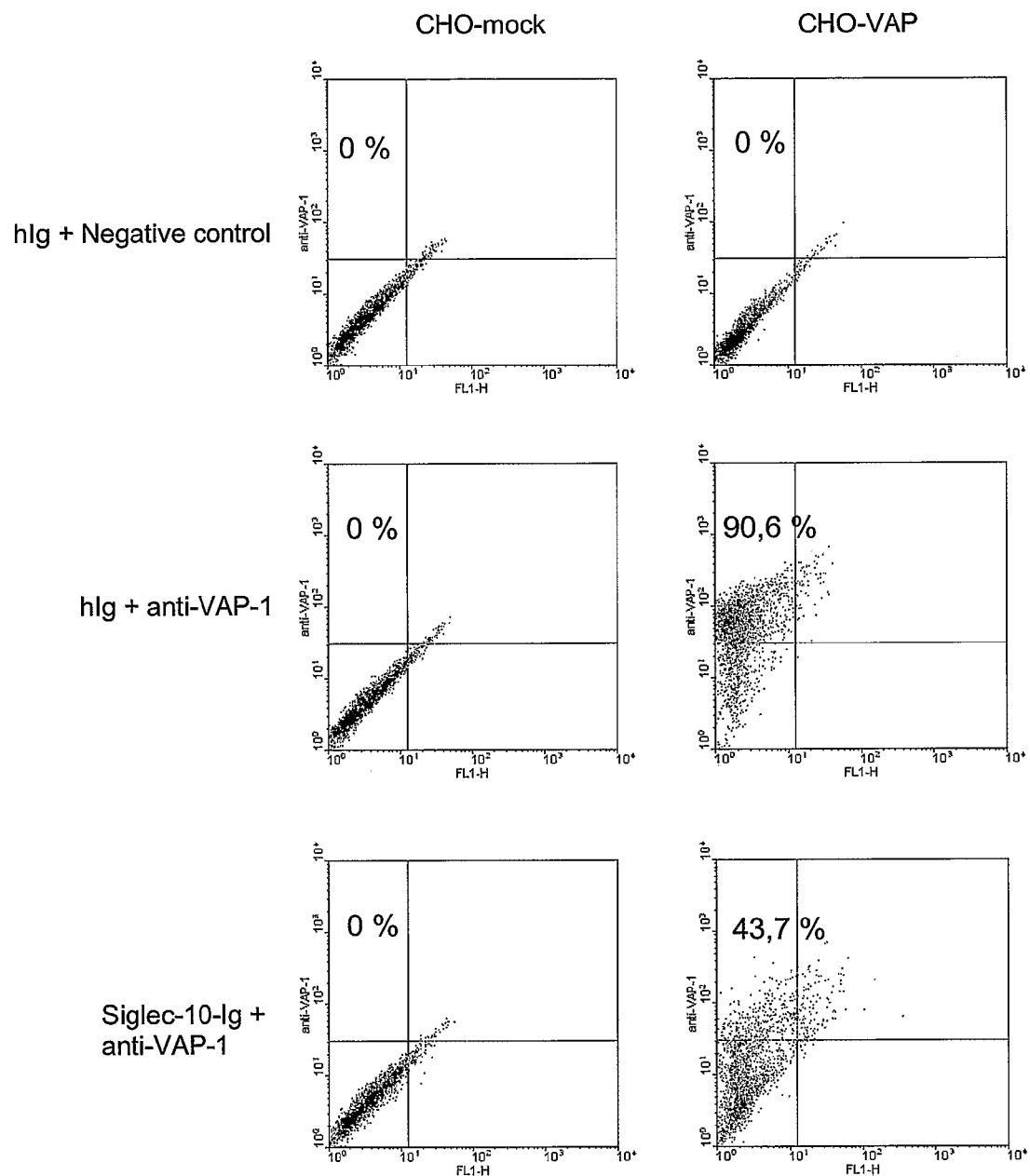
FIG. 4. Interaction between VAP-1 and Siglec-10 prevents the binding of anti-VAP-1 antibody to VAP-1. Cells expressing VAP-1 or control cells were first incubated with either human-Ig (hIg) or Siglec-10-Ig and after that stained with anti-VAP-1 or a negative control mAb. The cells were then analysed by flow cytometry. Percentages of cells positively stained with anti-VAP-1 mAb are shown in upper left quadrant.

Competitive stainings of cells expressing VAP-1 and control cells using anti-VAP-1 antibody, either in the presence of Siglec-10-Ig or human Ig, also suggests an interaction between VAP-1 and Siglec-10. When the cells expressing VAP-1 are incubated with control human Ig and with anti-VAP-1 antibody, 90.6% of the cells are positive, but when cells are first incubated with Siglec-10-Ig, only 43.7% of the cells are positive (FIG. 4). With negative control antibody the cells are negative and also when all the stainings are done with mock transfected cells. These data thus suggests that when VAP-1 expressing cells are incubated with Siglec-10-Ig, they interact, and the interaction between VAP-1 and Siglec-10 partly prevents the binding of anti-VAP-1 antibody to VAP-1 expressed on the cell surface. Moreover, these results suggest that the Siglec-10 binding site on VAP-1 is partially overlapping with the antibody binding site.

Interaction Between VAP-1 and Siglec-10 is not Sialic Acid Dependent

Figure 5:
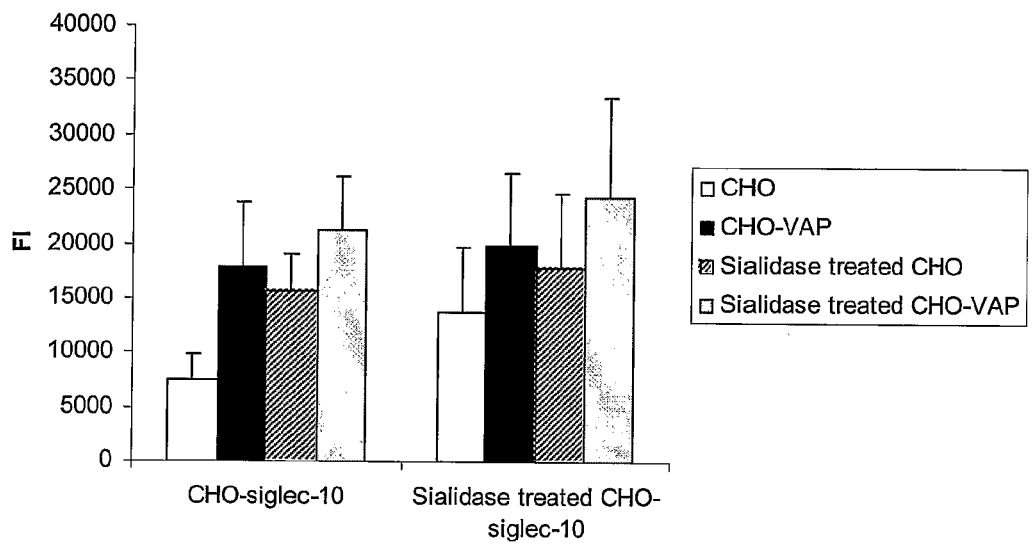
FIG. 5. The interaction between VAP-1 and Siglec-10 is not dependent on sialic acids on the surface of either VAP-1 or Siglec-10 expressing cells. Cells expressing VAP-1 and control cells were plated into 96-well tissue culture plate and allowed to reach confluence. Some of the cells expressing VAP-1 and control cells and cells expressing Siglec-10 were treated with sialidase to remove the sialic acids. After the sialidase treatment cells expressing Siglec-10 were labeled with a fluorescent dye and incubated in wells plated with cells expressing VAP-1 and control cells. Binding was detected with a fluorometer. The results are means of fluorescence intensities (FI)±SEM from four separate experiments each having duplicate wells.

Because VAP-1 is heavily sialylated and it is known that Siglecs bind to sialic acids we wanted to test, whether the interaction between VAP-1 and Siglec-10 is sialic acid dependent. We did adhesion assays between cells expressing VAP-1 and cells expressing Siglec-10 and treated either cells expressing VAP-1 with sialidase or cells expressing-Siglec-10 with sialidase. The sialidase treatment of Siglec-10 expressing cells did not alter the interaction between Siglec-10 and VAP-1 and the same was evident also when sialidase treatment was done to cells expressing VAP-1 (FIG. 5). On the other hand, sialidase treatment of cells appears to increase the background binding. Altogether, the results indicate that the interaction between VAP-1 and Siglec-10 is not dependent on sialic acids either on VAP-1 or on Siglec-10, but at the same time, when the sialic acids are removed, the non-specific binding increases.

Interaction Between VAP-1 and Siglec-10 Changes the Enzymatic Activity of VAP-1

Figure 6:
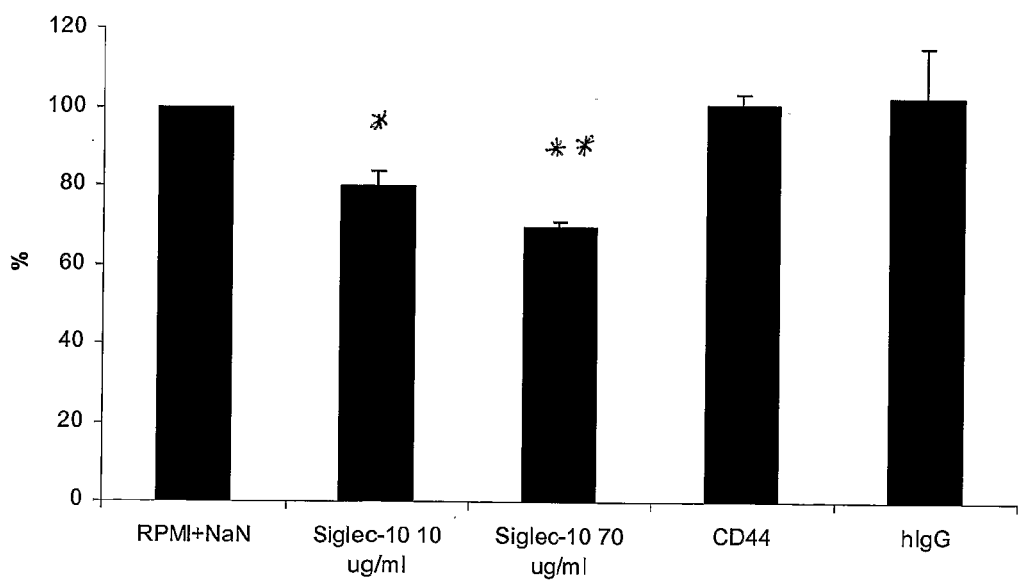
FIG. 6. Interaction between VAP-1 and Siglec-10 changes the enzymatic activity of VAP-1. CHO-VAP-1 cell lysate was incubated with Siglec-10-Ig-chimera or with controls and the enzymatic activity was determined using the radiochemical method. The mean activities±SEM from 2 separate experiments are shown. *$P<0.05$, **$P<0.01$.

The enzymatic activity of VAP-1 is known to have a role in recruiting leukocytes to sites of inflammation. Therefore, we wanted to elucidate, whether the interaction between VAP-1 and Siglec-10 has affects enzymatic activity of VAP-1. The isotopic enzyme assay showed that the SSAO activity of VAP-1 was significantly inhibited when allowed to interact with Siglec-10 (FIG. 6). A 20% inhibition of SSAO activity was already achieved using 10 µg/ml (~7 nM) of Siglec-10-Ig-chimera. Moreover, the inhibition of the SSAO activity was dose dependent, because by using 70 µg/ml (~50 nM) of Siglec-10-Ig-chimera, a 30% inhibition was obtained. Controls, CD44-Ig-chimera and human Ig, on the other hand, did not have an effect on the enzymatic activity of VAP-1. Our data thus suggest that the binding of Siglec-10 to VAP-1 interferes with the enzymatic activity of VAP-1.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. An isolated peptide having the amino acid sequence CVKWRGVVVC (SEQ ID NO. 1) or CWSFRNRVLC (SEQ ID NO. 2).

2. The peptide according to claim 1, said peptide constituting a portion of a leukocyte surface protein.

3. The peptide according to claim 1, said peptide constituting a portion of a protein belonging to the Siglec or ADAM group or to the CD58 glycoprotein.

4. The peptide according to claim 3, wherein the Siglec protein is Siglec-9.

5. The peptide according to claim 3 wherein the Siglec protein is Siglec-10.

6. The peptide according to claim 3, wherein the ADAM protein is ADAM 28.

7. A diagnostic composition for targeting the VAP-1 enzyme in vivo, said composition comprising a labeled peptide having the capability to bind to said enzyme, and wherein the peptide is as defined in claim 1.

8. A pharmaceutical composition for use to modulate the activity of VAP-1 enzyme, wherein said composition comprises:
   i) a peptide as defined in claim 1, or
   ii) the peptide of (i), said peptide being further conjugated to a therapeutically active agent.

9. The composition according to claim 8 wherein the therapeutically active agent is incorporated in a nanoparticle.

10. The composition according to claim 8 wherein the therapeutically active agent is a VAP-1 inhibitor.

* * * * *